United States Patent
Simopoulos et al.

(10) Patent No.: US 7,648,460 B2
(45) Date of Patent: Jan. 19, 2010

(54) MEDICAL DIAGNOSTIC IMAGING OPTIMIZATION BASED ON ANATOMY RECOGNITION

(75) Inventors: Constantine Simopoulos, San Francisco, CA (US); Shaohua Kevin Zhou, Plainsboro, NJ (US); Jin-hyeong Park, Princeton, NJ (US); Dorin Comaniciu, Princeton, NJ (US); Bogdan Georgescu, Plainsboro, NJ (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 304 days.

(21) Appl. No.: 11/513,675

(22) Filed: Aug. 30, 2006

(65) Prior Publication Data

US 2007/0055153 A1 Mar. 8, 2007

Related U.S. Application Data

(60) Provisional application No. 60/712,955, filed on Aug. 31, 2005.

(51) Int. Cl.
*A61B 17/00* (2006.01)
(52) U.S. Cl. .................................. 600/437; 600/443
(58) Field of Classification Search ............... 600/437
See application file for complete search history.

(56) References Cited

U.S. PATENT DOCUMENTS 7,092,749 B2 *  8/2006  Fowkes et al. .............. 600/407
7,286,707 B2 * 10/2007  Liu et al. ..................... 382/190
7,311,666 B2 * 12/2007  Stupp et al. ................. 600/300
2005/0096539 A1   5/2005  Leibig et al.
2005/0251013 A1* 11/2005  Krishnan et al. ............ 600/407
2006/0064017 A1   3/2006  Krishnan et al.

OTHER PUBLICATIONS

Paul Viola and Michael Jones, Rapid Object Detection using a Boosted Cascade of Simple Features, 2001, IEEE, vol. 1, pp. I-511-I518.*
Viola, P. and Jones, M., "Rapid Object Detection Using A Boosted Cascade Of Simple Features", IEEE (2001) ISBN 0-7695-1272-0/01.
Dietterich, T. and Bakiri, G., "Solving Multiclass Learning Problems via Error-Correcting Output Codes", Journal of Artificial Intelligence Research 2 (1995), pp. 263-286.
Ebadollahi, S. et al, "Automatic View Recognition In Echocardiogram Videos Using Parts-Based Representation," *IEEE CVPR*, (2004) pp. 2-9, ISBN 0-1063-6919/04.
Fei-Fei, L. and Perona, P., "A Bayesian Approach to Unsupervised One-Shot Learning of Object Categories", ICCV, (2003) pp. 1-8.
Freund, Y. and Schapire, R., "A decision-theoretic generalization of on-line learning and an application to boosting", AT&T Bell Laboratories, Murray Hill, NJ, (Sep. 20, 1995), pp. 1-34.

(Continued)

*Primary Examiner*—Long V Le
*Assistant Examiner*—Hien Nguyen (57) ABSTRACT

Anatomical information is identified from a medical image and/or used for controlling a medical diagnostic imaging system, such as an ultrasound system. To identify anatomical information from a medical image, a processor applies a multi-class classifier. The anatomical information is used to set an imaging parameter of the medical imaging system. The setting or identification may be used in combination or separately.

18 Claims, 3 Drawing Sheets

OTHER PUBLICATIONS

Friedman, J. et al, "Additive Logistic Regression: a Statistical View of Boosting", Dept. of Statistics, Stanford University, CA, (Aug. 20, 1998), pp. 1-45.

Krempp, S. et al., "Sequential Learning of Reusable Parts for Object Detection", CMLA, pp. 1-7, (2002).

Lazebnik et al., "Affine-Invariant Local Descriptors and Neighborhood Statistics for Texture Recognition", ICCV, (2003).

LeCun, Y. et al., "Learning Methods for Generic Object Recognition With Invariance To Pose And Lighting," *CVPR*, (2004).

Li, S. and Zhang, Z., "Floatboost Learning And Statistical Face Detection," *PAMI*, 26(9), (2004).

Lowe, D., "Object Recognition from Local Scale-Invariant Features", ICCV, (Sep. 1999).

Schapire, R. and Singer, Y. "Improved Boosting Algorithms Using Confidence-rated Predictions," Machine Learning, (1999), 37(3); pp. 297-336.

Tagare, H. et al, "Arrangement: A Spatial Relation Between Parts For Evaluating Similarity Of Tomograhic Section," *PAMI*, 17:880-893, (1995).

Torralba, A. et al., "Sharing features: efficient boosting procedures for multiclass detection", CVPR, 2004, 1-8 pages.

Tu, Z., "Probabilistic Boosting-Tree: Learning Discriminative Models for Classification, Recognition, and Clustering", ICCV, 2005.

Papageorgiou, C. et al, "A General Framework For Object Detection," *ICCV*, 1998.

Hastie, et al, "Data Mining, Interference, and Prediction", Springer Series in Statistics, (2001), pp. 270-271, and 412-420.

Doucet, et al, "Sequential Monte Carlo Methods in Practice", Statistics for Engineering and Information Science (2001), pp. 3-14.

\* cited by examiner

MEDICAL DIAGNOSTIC IMAGING OPTIMIZATION BASED ON ANATOMY RECOGNITION

RELATED APPLICATIONS

The present patent document claims the benefit of the filing date under 35 U.S.C. §119(e) of Provisional U.S. Patent Application Ser. No. 60/712,955, filed Aug. 31, 2005, which is hereby incorporated by reference.

BACKGROUND

The present embodiments relate to medical imaging. In particular, automated identification of anatomical structure and/or control of medical imaging are provided.

One type of medical imaging is ultrasound. Echocardiography is ultrasound imaging of the human heart. Echocardiography is a commonly used imaging modality to visualize the structure of the heart. Because the echo is often a 2D projection of the 3D human heart, standard views are captured to better visualize the cardiac structures. For example, in the apical four-chamber (A4C) view, all four cavities, namely left and right ventricles, and left and right atria, are present. In the apical two-chamber (A2C) view, only the left ventricle and the left atrium are present.

Acquired cardiac views often deviate from the standard views due to machine properties, the inter-patient variations, or the skill or preference of sonographers. The sonographer manually adjusts imaging parameters of the ultrasound system and transducer position for echocardiography, resulting in variation. An imaging configuration may be selected from a list of organs (presets) with predetermined settings of imaging parameters. However, the presets require keystrokes and interruption of the workflow to invoke new settings each time the anatomical view changes. In order to keep the list manageable, the list may not contain all the variations and subcases. For example, in echocardiography, there are many views or imaging planes even though the same organ is imaged (heart). For each view, the optimal location of the color Doppler panbox is different.

After acquiring images based on the settings, the views may be classified automatically. However, detection of multiple objects is challenging. In U.S. Pat. No. 7,092,749, template modeling or matching is used to identify different structures. Trained classifiers have also been used. Most existing approaches train a separate binary classifier for each object against the background, and scan the input image for objects. Using different classifiers for different objects has inherent disadvantages. In training, the training complexity increases linearly with the number of classes. In testing, it is likely that several classifiers identify different structure at the same location. Due to the difficulty in comparing responses among these classifiers, determining the actual object needs additional work, such as training pairwise classifiers between two object classes. Also, evaluating multiple binary classifiers is a time-consuming process.

BRIEF SUMMARY

By way of introduction, the preferred embodiments described below include methods, computer readable media and systems for identifying information from a medical image and/or for controlling a medical diagnostic imaging system, such as an ultrasound system. To identify anatomical information from a medical image, a processor applies a trained classifier, such as a multi-class classifier. The anatomical information is used to set an imaging parameter of the medical imaging system. The setting or identification may be used in combination or separately.

In a first aspect, a method is provided for controlling a medical diagnostic ultrasound imaging system. An ultrasound image is obtained. A processor identifies an anatomical feature in the image with a trained classifier. The processor sets an imaging value as a function of the anatomical feature. Subsequent imaging with the medical diagnostic ultrasound system is responsive to the imaging value set as the function of the anatomical feature.

In a second aspect, a computer readable storage medium has stored therein data representing instructions executable by a programmed processor for controlling a medical imaging system. The storage medium includes instructions for deriving anatomical information from a medical image from learned feature vectors, and setting at least one imaging parameter of the medical imaging system as a function of the anatomical information.

In a third aspect, a medical diagnostic imaging system includes a memory operable to store a medical image. A processor is operable to apply a classifier based on machine learning to the medical image. The classifier is operable to identify a canonical view, tissue structure, flow pattern or combinations thereof from the medical image. The processor is operable to control imaging as a function of the view, structure, pattern or combination thereof.

In a fourth aspect, a method is provided for identifying information from a medical image. A multi-class classifier is applied to the medical image. A particular canonical view, tissue structure, flow pattern or combinations thereof is identified from the medical image as a function of applying the multi-class classifier.

In a fifth aspect, a computer readable storage medium has stored therein data representing instructions executable by a programmed processor for identifying information from a medical image. The storage medium includes instructions for applying a multi-class classifier to the medical image, and identifying a particular canonical view, tissue structure, flow pattern or combinations thereof from the medical image as a function of applying the multi-class classifier.

The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

A classifier recognizes the anatomy being imaged. The recognition may be in real-time, during a same imaging session or while the imaging is occurring, but may occur later. System controls for optimal imaging and measurements are automatically adjusted based on the anatomy. For example, automatic adjustment of ultrasound system controls occurs where the optimal settings depend on the anatomy being imaged. The anatomy may indicate a location appropriate for the color panbox and the Doppler gate, such as over a valve for flow measurements. The B-mode display depth and the B-mode frequency may be set based on the anatomy. By automating various image optimization tasks, workflow may be improved. Consistent quality of imaging may be increased or achieved by reducing user variability. Automatic measurements can also be performed in the background on relevant anatomy without the user having to push a button. For example, when the femur of a fetus shows up in the image, the length is measured automatically and is added to the metadata.

In one embodiment, the anatomy is classified with an image based multi-class boosting classifier. For example, cardiac views for an echocardiographic sequence are treated as multi-class object detection. One multi-class classifier is trained using the LogitBoost algorithm. To utilize the fact that, in the midst of boosting, one class is fully separated from the remaining classes, a tree structure that focuses on the remaining classes is learnt to improve learning and application efficiency. To accommodate the large number of background images, a cascade of boosted multi-class classifiers is used. The multi-class classifier may be able to simultaneously detect and classify multiple objects while rejecting the background class quickly.

Figure 1:
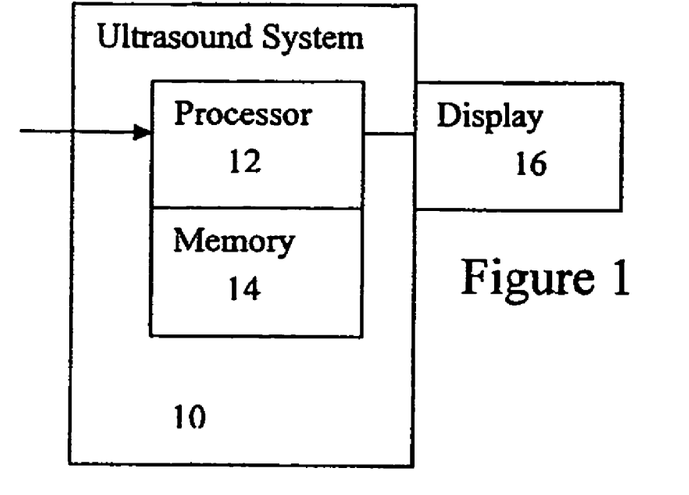
FIG. 1 is a block diagram of one embodiment of a medical imaging system.

FIG. 1 shows a medical diagnostic imaging system 10 for identifying anatomical features, controlling imaging as a function of imaged anatomical features, and/or imaging as a function of anatomical information. The system 10 is a medical diagnostic ultrasound imaging system, but may be a computer, workstation, database, server, X-ray device, computed tomography device, magnetic resonance device, positron emission device, or other system. The system 10 includes a processor 12, a memory 14, and a display 16. Additional, different, or fewer components may be provided.

The memory 14 is a buffer, cache, RAM, removable media, hard drive, magnetic, optical, or other now known or later developed memory. The memory 14 is a single device or group of two or more devices. The memory 14 is shown within the system 10, but may be outside or remote from other components of the system 10.

The memory 14 stores medical image data, such as ultrasound, X-ray, MRI, CT or PET image data. For example, the memory 14 stores flow (e.g., velocity, energy or both) and/or B-mode ultrasound data. Alternatively, the medical image data is transferred to the processor 12 from another device. The medical image data is a single two- or three-dimensional data set, or a sequence of such sets. For example, a sequence of images over a portion, one, or more heart cycles of the heart are stored. A plurality of sets may be provided, such as associated with imaging a same person, organ or region from different angles or locations.

The memory 14 is additionally or alternatively a computer readable storage medium with processing instructions. Data representing instructions executable by the programmed processor 12 for controlling a medical imaging system or for identifying information from a medical image is stored.

The instructions for implementing the processes, methods and/or techniques discussed herein are provided on computer-readable storage media or memories, such as a cache, buffer, RAM, removable media, hard drive or other computer readable storage media. Computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone or in combination. Likewise, processing strategies may include multiprocessing, multitasking, parallel processing and the like. In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU, or system.

The processor 12 is a general processor, digital signal processor, application specific integrated circuit, field programmable gate array, digital circuit, analog circuit or other now known or later developed device for processing medical image data. The processor 12 is a single device, a plurality of devices, or a network. For more than one device, parallel or sequential division of processing may be used. In one embodiment, the processor 12 is a control processor or other processor of a medical diagnostic imaging system, such as a medical diagnostic ultrasound imaging system processor. The processor 12 operates pursuant to stored instructions to perform various acts described herein, such as obtaining data, deriving anatomical information, setting an imaging parameter and/or controlling imaging.

In one embodiment, the processor 12 applies a classifier to a medical image. Any classifier may be applied, such as a model based classifier or a learned classifier or classifier based on machine learning. For learned classifiers, binary or multi-class classifiers may be used, such as Bayesian or neural network classifiers. In one embodiment, a multi-class boosting classifier with a tree and cascade structure is used. The classifier is instructions, a matrix, a learned code, or other software and/or hardware for distinguishing between information in a medical image. Learned feature vectors are used to classify the anatomy. For example, the classifier identifies a canonical view, tissue structure, flow pattern or combinations thereof from a medical image or sequence of images. In cardiac imaging, the classifier may identify cardiac structure associated with a particular view of a heart. The view is a common or standard view (e.g., apical four chamber, apical two chamber, left parasternal, or sub-coastal), but other views may be recognized. The cardiac structure is the heart walls or other structure defining the view or a structure associated with the view. For example, a valve associated with an apical four chamber view is identified from an identified apical four chamber view.

In an alternative or additional embodiment, the processor 12 controls imaging as a function of the view, structure, pattern, combinations thereof or other anatomical information. The processor 12 sets one or more imaging parameters based on the anatomical information. For example, an apical two chamber view is identified by the processor 12. A position for Doppler or flow imaging is set based on the view, such as positioning a color pan box over a chamber, both chambers, a valve or other locations. The transmit sequence, scan line location or other processing is altered to provide color or flow information for the selected region. As another example, a heart chamber tissue structure is identified. The B-mode display depth is set to fully scan the heart walls of the chamber while minimizing extraneous scan depth. The B-mode frequency may also be set to provide the desired ultrasound penetration with a highest resolution for the given depth. Other imaging parameters may be set, such as filtering, beamforming, scanning, detecting, estimating, scan converting, displaying, or combinations thereof. The anatomical information may be used to select an imaging preset or group of all, many, most, or some imaging parameters for a particular type of imaging or anatomy (e.g., an A4C preset).

Figure 2:
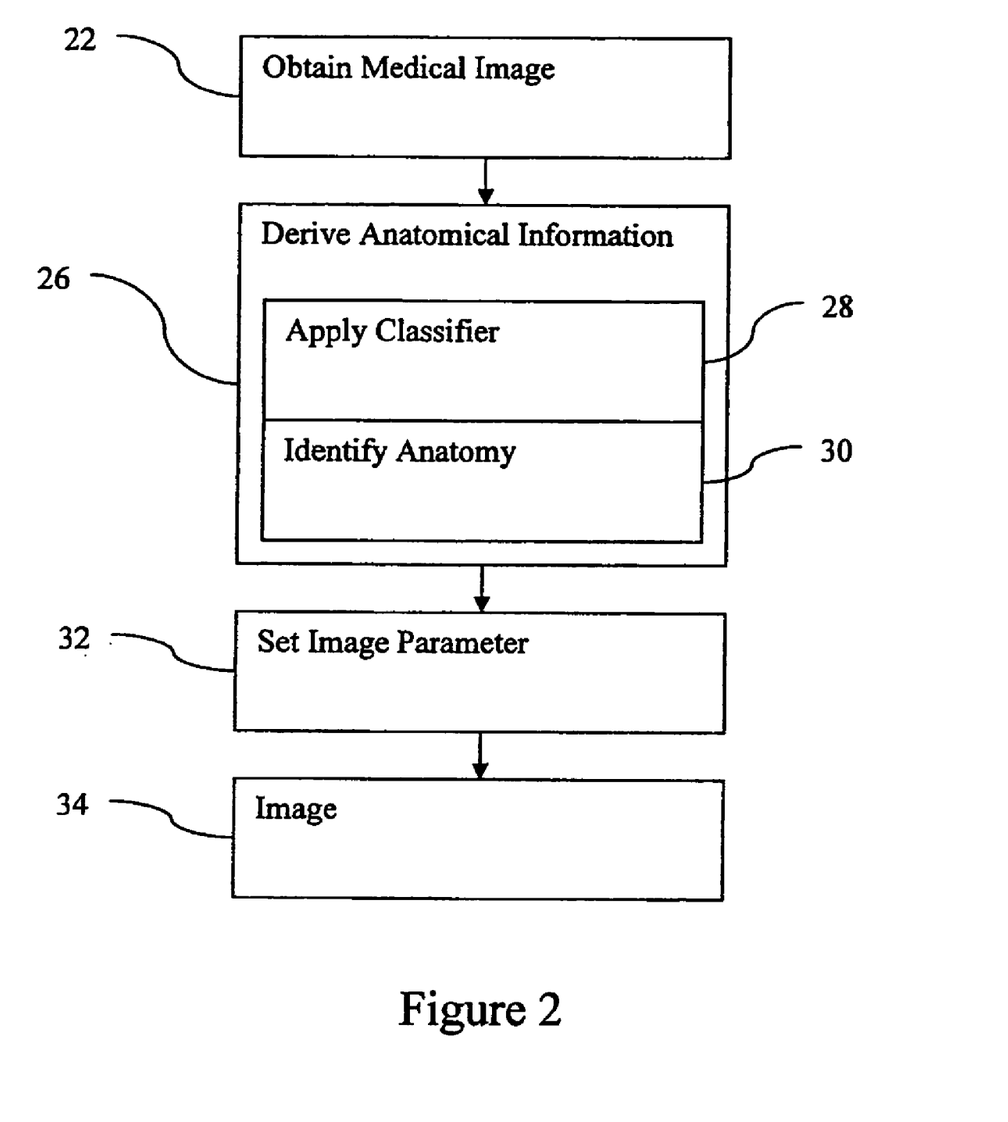
FIG. 2 is a flow chart diagram of embodiments of methods for identifying anatomical information and setting imaging parameters as a function of anatomical information.

FIG. 2 shows a method for controlling a medical diagnostic imaging system, such as an ultrasound system. The method is implemented by a medical diagnostic imaging system, a review station, a workstation, a computer, a PACS station, a server, combinations thereof, or other device for image processing medical image data. For example, the system or computer readable media shown in FIG. 1 implements the method, but other systems may be used. The method is implemented in the order shown or a different order. Additional, different, or fewer acts may be performed. For example, acts 22 and 34 are optional. As another example, act 26 is performed without acts 22, 32 and/or 34.

In act 22, one or more medical images are obtained. The medical images are obtained by real-time scanning. For example, an ultrasound image or sequence of images are obtained by scanning a two or three-dimensional region of a patient. The image or image data corresponds to a displayed image (e.g., detected and scan converted ultrasound data) or data for generating an image (e.g., beamformed or other acquired data for generating a display with further processing). In alternative embodiments, the medical image is obtained from a transfer, such as over a network, from a memory, or from a database. The transferred medical image data is from a previous acquisition or is obtained in real-time or during an imaging session.

The medical image represents a region of a patient. The region includes tissue, fluid or other structures. Different structures or types of structures react to the imaging modality differently. For example, heart muscle tissue moves, but slowly as compared to fluid. The temporal reaction results in different image data. The shape of a structure or spatial aspect may be reflected in the image data.

In act 26, anatomical information is derived from the medical image. The anatomical information is derived from a single image or a sequence of images. For example, the shape, the position of tissue over time, flow pattern, or other characteristic may indicate anatomical information. Anatomical information includes views, organs, structure, features, patterns, tissue type, or other information.

As represented by act 28, the anatomical information is derived by applying a classifier. The classifier identifies anatomy in act 30 from the medical image. By deriving anatomical information from the medical image, a processor may identify an anatomical feature in the image.

In act 28, the classifier is any now known or later developed classifier for extracting anatomical information from a medical image. The classifier is a single class or binary classifier, collection of different classifiers, cascaded classifiers, hierarchal classifier, multi-class classifier, model based classifier, classifier based on machine learning, other classifier, or combinations thereof. In one embodiment, the classifier is a multi-class classifier. The multi-class classifier is trained from a training data set using a computer. Multi-class classifiers include CART, K-nearest neighbors, neural network (e.g., multi-layer perceptron), mixture models, or others.

The multi-class classifier may include several binary classifications combined for a final decision. Different combinations may be used, such as "one vs. the rest" assuming that one class is separated from the remaining classes or one vs. one assuming that pairwise binary classifiers are learned. The AdaBoost algorithm is an algorithm that learns a binary classifier. The AdaBoost algorithm may be extended to handle a multi-class problem, the so-called AdaBoost.MH algorithm by reducing multi-class to binary. A multi-class boosting algorithm where no conversion from multi-class to binary is necessary may be used. Error-correcting output code (EOCC) may be used. In EOCC, because each class is assigned a unique binary string which is computed using binary classifiers, again the multi-class problem is converted to binary ones. Other multi-class or binary classifiers may be used.

The classifier is a computer learnt classifier, but may be programmed manually. In an alternative to learning-based, the classifier performs object recognition using correlation of feature points and/or parts to a template or model, such as disclosed in U.S. Pat. No. 7,092,749, the disclosure of which is incorporated herein by reference. For learning-based approaches, the classifier is taught to detect objects or information associated with anatomy. For example, the AdaBoost algorithm selectively combines into a strong committee of weak learners based on Haar-like local rectangle features whose rapid computation is enabled by the use of an integral image. A cascade structure may deal with rare event detection. The FloatBoost, a variant of the AdaBoost, may address multiview detection. Multiple objects may be dealt with by training a multi-class classifier with the cascade structure. The classifier learns various feature vectors for distinguishing between classes.

Because the strategy of learning different binary classifiers for different objects has the scalability issue as each classifier is trained and run independently, sharing features may overcome scalability for learning different binary classifiers for different objects. During training, the different classifiers maximally share the same set of features. As a consequence, the performance may be improved given the same modeling complexity. The final training outputs are again separate binary classifiers. Alternatively, a multi-class classifier is directly trained using boosting, which may share features at each round of boosting.

A probabilistic boosting tree (PBT), which unifies classification, recognition, and clustering into one treatment, may be used. The PBT, which is a binary tree, naturally targets a two-class setting by iteratively learning a strong classifier at each tree node. The training data are subsequently parsed into the left and right node at the next tree level. To deal with a multi-class problem, the multi-class problem is converted into a two-class problem by first finding the optimal feature that divides all remaining training examples into two parts and then use the two-class PBT to learn the classifier. Alternatively, a tree structure is trained, but in a different approach than with a PBT. Other classifiers include a general object detection frame based on a support vector machine or convolutional of a neural network trained to deal with multiple object classification.

Feature vectors for the classifier are input by the user and/or learnt. For example, the feature vectors are selected using a boosting framework or are learned from boosting.

One particular embodiment is an image-based multi-class boosting based classifier. A multi-class classifier is trained using the LogitBoost or other boosting algorithm. The LogitBoost algorithm combines weak learners (i.e., feature vectors) into a strong classifier. The weak learners are associated with the Haar-like local rectangle or other features for fast computations. Instead of using the simple decision stump (or regression stump), the use of piecewise constant function (e.g., step function) may enhance the modeling power of the weak learners.

Suppose a (J+1)-class classification problem. Classes {C1, C2, ..., CJ} stand for J objects and class C0 stands for the background class or none-of-the above. The training set for the class Cj (j=0; 1; : : : ; J) is denoted by:

$$S_j = \{x_1^{[j]}, x_2^{[j]}, \ldots, x_{n_j}^{[j]}\}$$

The training sets for the classes are pooled together to form a big training set {x1, x2, ..., xN}, where $$N = \sum_{j=0}^{J} n_j.$$

The class label for each data point xi is represented by a J+1 vector:

$$y_i^* = [y_{i0}^*, y_{i1}^*, \ldots, y_{iJ}^*] \qquad (1)$$

If the true label for xi is c, then:

$$y_{ij}^* = [j = c] = \begin{cases} 1 & \text{if } j = c \\ 0 & \text{otherwise} \end{cases} \qquad (2)$$

where [90] is an indicator function of the predicate π. If π holds, then [π]=1, otherwise, [π]=0.

In one embodiment, the LogitBoost algorithm is used. The output of the LogitBoost algorithm is a set of (J+1) learned response functions: {$F_j(x)$; j=0, 1, ..., J}. Each $F_j(x)$ is a linear combination of the set of weak learners (e.g., feature vectors with small probability), thereby the $F_j(x)$ functions automatically share features. The LogitBoost algorithm is illustrated by:

LogitBoost(J+1 classes)

1. Start with weights $w_{ij}$=1/N, i=1, 2, ..., N, j=0, 1, ..., J, $F_j(x)$=0, and p, (x)–1/(J+1) ∀$_j$.
2. Repeat for m=1, 2, ..., M:
   Repeat for j=0, 1, ..., J:
   Compute working responses and weights in the j$^{th}$ class $$z_{ij} = \frac{y_{ij}^* - p_j(x_i)}{p_j(x_i)(1 - p_j(x_i))}; \qquad (5)$$

$$w_{ij} = p_j(x_i)(1 - p_j(x_i)). \qquad (6)$$

(Δ) Fit the function $f_{mj}(x)$ by a weighted least-squares regression of $z_{ij}$ to $x_t$ with weights $w_{ij}$.

Set $f_{mj}(x) \leftarrow \frac{J}{J+1}\left(f_{mj}(x) - \frac{1}{J+1}\sum_{k=0}^{J} f_{mk}(x)\right)$, and $F_j(x) \leftarrow F_j(x) + f_{mj}(x)$.

Update $p_j(x) \propto \exp(F_j(x))$.
3. Output the classifier arg max$_j F_j(x)$.

The LogitBoost algorithm fits an additive symmetric logistic model to achieve maximum likelihood using adaptive quasi-Newton steps. The final classification result is determined as:

$$j = \arg\max_{j=0,1,\ldots,J} F_j(x) \qquad (3)$$

The LogitBoost algorithm provides a way to calculate the posterior distribution of class label:

$$p_j(x) = \frac{\exp(F_j(x))}{\sum_{k=0}^{J} \exp(F_k(x))} = \frac{\exp(F_j'(x))}{1 + \sum_{k=1}^{J} \exp(F_k'(x))}, \qquad (4)$$

where $F_j'(x) = F_j(x) - F_0(x)$

The step (Δ) of the LogitBoost algorithm solves the following optimization problem:

$$f_{mj} = \underset{f \in F}{\operatorname{argmin}} \sum_{i=1}^{N} w_{ij}|z_{ij} - f(x_i)|^2. \qquad (7)$$

where F is a dictionary set.

The dictionary set is a structural component in boosting since the dictionary set determines the space where the output classifier function resides. Piecewise constant functions may be used as the elements of the dictionary set. A piecewise constant function that is associated with a feature function quantizes the feature response in a piecewise fashion:

$$f(x) = \sum_{k=1}^{K} a_k [h(x) \in R_k]; R_k = (\theta_{k-1}, \theta_k]. \qquad (8)$$

where [.] is an indicator function, h(x) is the feature (response) function, and {Rk; k=1, ..., K} are the intervals that divide the whole real line with $\theta_0 = -\infty$ and $\theta_K = \infty$.

Figure 4:
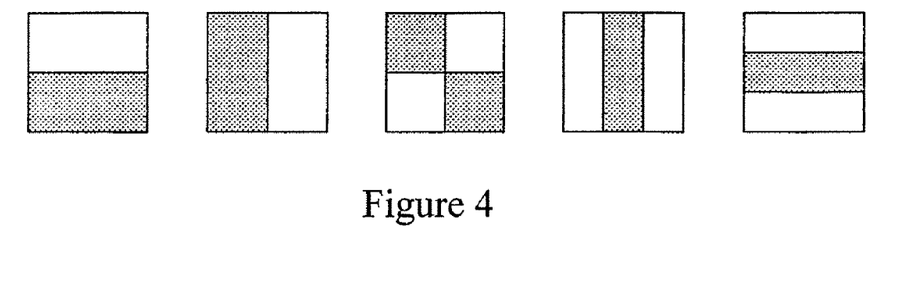
FIG. 4 is a graphical representation of directional filters in various embodiments.

A linear feature may be used, such as h(x)=g ⊗x, where g defines the feature and ⊗denotes a convolution. The linear feature attempts to identify edges in an image. Other features may be used, such as templates based on expected patterns. Since every function in the dictionary set is associated with a unique feature, this step allows boosting to operate as an oracle that selects the most relevant visual features. For linear features, local rectangle features whose responses can be rapidly evaluated by an integral image (e.g., sum of all pixels above and to the left of a given pixel) may be used. The g function that defines the feature is parameterized as g=r, c, w, h, t where (r, c) is the rectangle center, (w, h) is the rectangle size, and t is the feature type. FIG. 4 shows five feature types used in one embodiment. The medical image is filtered with the different shapes to identify different edges (i.e., wavelet decomposition of the medical image data). For each pixel of the medical image in an embodiment using the five filters of FIG. 4, five feature values are provided. Fewer or more features values may be used. The piecewise constant function is in the following form $f(x)=f(x, r, c, w, h, t)$. The intervals $R_k$ for each rectangle feature are empirically determined before training. One way is to find the minimum and maximum responses for each rectangle feature across the entire training sample, and then uniformly divide ranger for the feature into K intervals. More or fewer than five feature types may be used. Other features may be used.

Equation (7) now becomes:

$$f_{mj} = \arg\min_{r,c,w,h,t} \sum_{i=1}^{N} w_{ij}|z_{ij} - f(x_i; r, c, w, h, t)|^2. \tag{9}$$

For a given configuration (r, c, w, h, t), the optimal values of a are computed as:

$$a_k = \frac{\sum_{i=1}^{N} w_{ij} z_{ij}[(g \otimes x_i) \in R_k]}{\sum_{i=1}^{N} w_{ij}[(g \otimes x_i) \in R_k]}. \tag{10}$$

In the step (Δ) in the LogitBoost algorithm, the most relevant feature with the smallest error is singled out to maximally reduce the classification error. Simple binary regression stumps may be used. Alternatively, the piecewise constant function combines multiple binary regression stumps, enhancing the modeling capability of the weak learners and consequently improving training speed.

As an alternative or in addition to a multi-class learned classifier, other structures may be provided. In one embodiment, the multi-class classifier includes a tree and/or a cascade structure.

Figure 5:
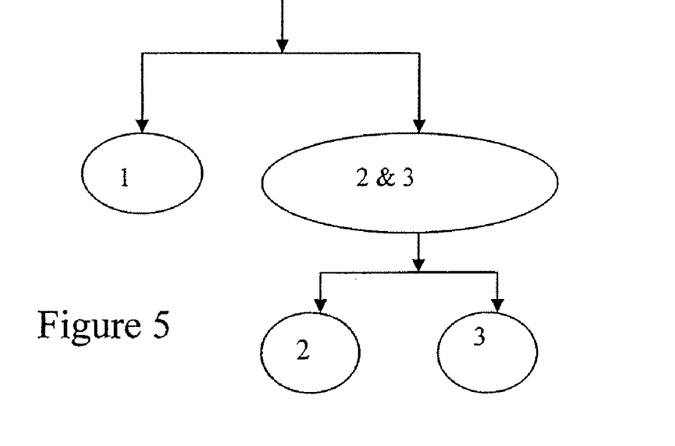
FIG. 5 is a graphical representation of one embodiment of a tree structure for classifying.

A tree structure is learned and may offer efficiency in both training and application. Often, in the midst of boosting a multi-class classifier, one class (or several classes) has been completely separated from the remaining ones and further boosting yields no additional improvement in terms of the classification accuracy. For efficient training, a tree structure is trained. To take advantage of this fact, a tree structure is trained by focusing on the remaining classes to improve learning efficiency. Posterior probabilities or known distributions may be computed, such as by correlating anterior probabilities together.

FIG. 5 gives a simple example to illustrate the tree training. Suppose a 3-class problem (C1, C2, and C3). After several boosting iterations, the class C1 has been classified correctly. Training is stopped and the output functions are stored as $\{F_{1j}(x); j=1, 2, 3\}$, which forms the first layer (e.g., upper layer of FIG. 5) of the tree that merges the classes C2 and C3. For the second layer of the tree, a binary classifier is trained that separates C2 and C3. The output functions are stored as $\{F_{2j}(x); j=2, 3\}$.

To calculate the posterior probability of the class label, the posterior probability for each tree layer is computed. For example, for the first layer, $$p_1(1 \mid x) = \frac{\exp(F_{1,1}(x))}{\sum_{j=1}^{3} \exp(F_{1,j}(x))}; p_1(2, 3 \mid x) = 1 - p_1(1 \mid x). \tag{11}$$

is computed. For the second layer, $$p_2(2 \mid x) = \frac{\exp(F_{2,2}(x))}{\sum_{j=2}^{3} \exp(F_{2,j}(x))}; p_2(3 \mid x) = 1 - p_2(2 \mid x). \tag{12}$$

is computed. Finally, the overall posterior probabilities are:

$$p(1|x)=p_1(1|x); p(2|x)=p_1(2,3|x)p_2(2|x); \tag{13}$$

$$p(3|x)=p_1(2,3|x)p_2(3|x). \tag{14}$$

It is easy to verify that $$\sum_{j=1}^{3} (j \mid x) = 1.$$

The 3-class example may be generalized to an arbitrary multi-class problem. The 'divide-and-merge' strategy is repeated. A multi-class classifier is learned to divide each merged class. After the classifier is learned, those 'easy' classes are separated from the remaining classes that are merged into one class. Similarly, the posterior calculation can be carried out.

In an alternative embodiment, PBT is used. When 'dividing' at each tree node, the PBT first converts a multi-class task to a binary one based on an optimal feature and then invokes boosting to learn a binary classifier. Conversely for the LogitBoost tree example, such a conversion is not performed and a multi-class classifier is learned. Second, there is no 'merging' operation in the PBT. The samples are divided till there is no further ambiguity. Conversely, the LogitBoost tree example operates at a class level rather than a sample level as in the PBT.

Figure 6:
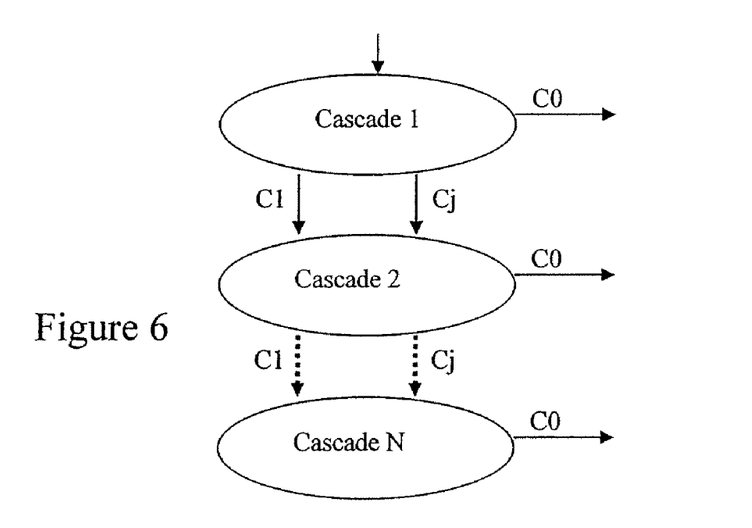
FIG. 6 is a graphical representation of one embodiment of a cascade structure for classifying.

To handle the background classes with many examples, a cascade training procedure may be used. A cascade of boosted multi-class strong classifiers may result. The cascade of classifiers provides a unified algorithm able to detect and classify multiple objects while rejecting the background classes. The cascade structure corresponds to a degenerate decision tree. Such a scenario presents an unbalanced nature of data samples. The background class has voluminous samples because all data points not belonging to the object classes belong to the background class. FIG. 6 shows a cascade of boosted multi-class classifiers. To examine more background examples, only those background examples that pass the early stages of the cascade are used for training a current stage.

Alternatively, negative bootstrapping in the neural network may be used. The learned strong classifier for each stage is adjusted to reach a desired detection rate. For example, the strong classifier threshold is changed.

In the embodiment of FIG. 6, a cascade of boosted multiclass classifiers is trained. The examples for the background class fed to the first stage are randomly cropped, but actual or common background data may be used. To train a cascade of boosted multi-class classifiers, the training examples for class $\{C1, C2, \ldots, CJ\}$ may succeed the available stages. The response function $F_j(x)$ is changed. One simple solution is to add a constant shift $T_0$ to the output function of the background class, $F_0(x)$. The value of $T_0$ is chosen to guarantee the desired detection rate. The concept of the detection rate is applied to all classes except the background class.

Suppose that the desired rate is $1-\alpha$, $T_0$ is chosen such that:

$$F_i(x) \geq F_0(x) + T_0; x \in S_i = \{x_1^{[i]}, x_2^{[i]}, \ldots, x_{n_i}^{[i]}\} \quad (15)$$

is valid for $$\left\lfloor \left(\sum_{j=1}^{J} n_j\right) * (1-\alpha) + 0.5 \right\rfloor$$

times. In other words, $T_0$ is the $\alpha$ percentile of the values: $\{F'_j(x)=F_j(x)-F_0(x); x \in S_j, j=1,2,\ldots,J\}$.

The cascade structure is used during application of the classifier to detect an anatomical object. Anatomical objects of interest are detected from a medical image. The medical image is scanned. A window W that defines a region of interest slides in the space of $(x, y, \mu, s)$, where $(x, y)$, $\mu$, and s are the center, orientation, and scale of the window, respectively. Denote the set of all these windows by W:

$$W = \left\{ W \mid p_0^{(n)}(W) < \max_{j+1\ldots} p_j^{(n)}(W); n = 1, \ldots, N_{cas} \right\}. \quad (16)$$

where $p^{(n)}_j$ is the posterior probability of W being class j when the boosted multi-class classifier for the nth cascade is used, and $N_{cas}$ is the number of stages in the cascade. In the case when multiple objects are present in the image, each window in the above set is classified, and assigned a class label. Those windows with severe overlapping are post-processed. In the case when only one final decision is needed, such as cardiac view classification, ad hoc fusion strategies, such as majority voting, may be used. Only windows that pass all stages of the cascade are subject to final classification.

The tree and cascade structures are different concepts. The tree structure is a multi-class classifier, while the cascade consists of several stages of multi-class classifiers. The two structures may be combined. Alternatively, only a tree, only a cascade or neither structure is used in the classifier.

The classifier derives the anatomical information from the medical image, such as a medical diagnostic ultrasound image. The anatomical information is associated with any organ or other structure, such as with the heat. Any anatomical information may be identified, such as identifying cardiac structure associated with a particular view of a heart, a heart valve, a heart wall, a chamber, a canonical view, a tissue structure, a flow pattern, or combinations thereof.

For example, an echocardiographic view classification is provided. An echocardiographic video in a DICOM or other format is classified into three or more classes, such as the A4C and A2C views along with the background class. Other views, such as other canonical views, may be classified. The classes are classified using a learned cascade of multi-class strong classifiers. The A2C and A4C views are similar to each other and may be hard to discriminate. An image is classified without considering temporal information to reduce computation time, but temporal information may be used. Reduced computation may allow for more rapid classification, such as associated with real-time classification during imaging or scanning. One or more end-diastolic (ED) image frames are used for classification. The ED frame is characterized by the fact that the heart is mostly dilated. Also, the ED frame index is directly coded in the DICOM header. In alternative embodiments, other frames from one or more portions of the hearth cycle are used.

To create the classifier, training data is collected. Multi-class boosting training is performed with the training data. The training data includes A2C images or sequences and A4C images or sequences. Template layouts for the two views highlight their characteristic structures. The template is designed based on the left ventricle (LV) orientation and size. Specifically, for the A4C view, the template contains four chambers. For the A2C view, the template contains two chambers.

The LV endocardium is annotated or positioned to align the data for the different images of the training data and reduce the appearance variation. The annotation is performed manually or automatically. Given a training video sequence and a corresponding LV annotation, the template image is cropped according to the template layout and rescaled to a canonical size. For example, the LV contour is identified and a bounding box just enclosing the contour is formed. A template box is oriented and positioned based on the bounding box. The portions outside of the template box may be discarded from the image data or classification processing.

Given a video sequence, training images are collected from any number of frames, such as five frames (i.e., the ED-2 frame to ED+2 frame). By perturbing the template bounding box by a small amount around its center and in width, height, and angle, additional positives may be collected.

Negative training images are collected outside the perturbing range for positives. Any source of negative images may be used, such as scans associated with other views or a non-standard view.

The training data set is used to train a multi-class classifier with boosting. Using the Haar-like local rectangle features shown in FIG. 4, the medical image is filtered. Local high frequency components in various directions and resolutions are output. The output of each of the filters is a scalar value formed by subtracting the sum of the intensity values in the white rectangle(s) from that of the grey rectangle(s). The output value indicates the magnitude of a high frequency of the local region. By varying the type, location, and size of the filter, a large set of output data is generated.

A cascade of two multi-class classifiers are trained, but a larger number of cascades may be used. For each stage of the cascade, a tree structure is trained if applicable. To train the first cascade, negative samples are randomly selected twice or other number more than the positives. To train the second cascade, negative bootstrapping or other process may be used.

After training, the resulting classifier is applied to one or more medical images. For example, during online or real-time classification, the ED frames of an echocardiographic video sequence are classified.

The anatomical information is encoded based on a template. The image is searched based on the template information, localizing the chambers. Given a sequence of medical images, a search from the left-top corner to the right-bottom corner is performed by changing the width, height, and angle of a template box. The search is performed in a pyramid structure, with a coarse search on a lower resolution or decimated image and a refined search on a higher resolution image based on the results of the coarse search. This exhaustive search approach may yield multiple results of detections and classifications, especially around the correct view location. The search identifies one or more relevant regions of each medical image.

The search is performed by moving the template box. For each search location, features are provided by filtering. The regions of the medical image are filtered to identify high frequency content. For each region or window, W, the high frequency content is used for classification. The high frequency content is input into a classifier trained from high frequency content of training data.

The ED frame is classified into one of the trained views by combining the results of the windows. Any combination or fusion may be used, such as classifying according to the majority or most frequent class. In one embodiment, a multiple hypotheses fusion approach based on majority voting is used. If the system yields multiple hypotheses (classification results), the number of classification results of each view is computed and the final view is determined according to the maximum number of view classification results. If the numbers are the same, a simple tie-break rule based on the mean of all the posterior probabilities the classifier provides is used. The classification result of the ED frame represents the final view of the echocardiographic video sequence.

Other anatomical information may be derived in act 26. For example, once a view is determined, the template is used to define the location structures associated with the view, such as a valve. Alternatively, the structures are identified by classification. The classifier outputs the anatomical information.

In act 32, the value of one or more imaging parameters are set. A processor automatically controls the medical imaging system as a function of the anatomical information, such as an anatomical feature. For example, imaging or scanning is controlled as a function of the particular canonical view, tissue structure, flow pattern, other anatomical information, or combination thereof. The medical imaging system operates to scan a patient and generate medical images in response to one or more settings for imaging parameters.

Figure 3:
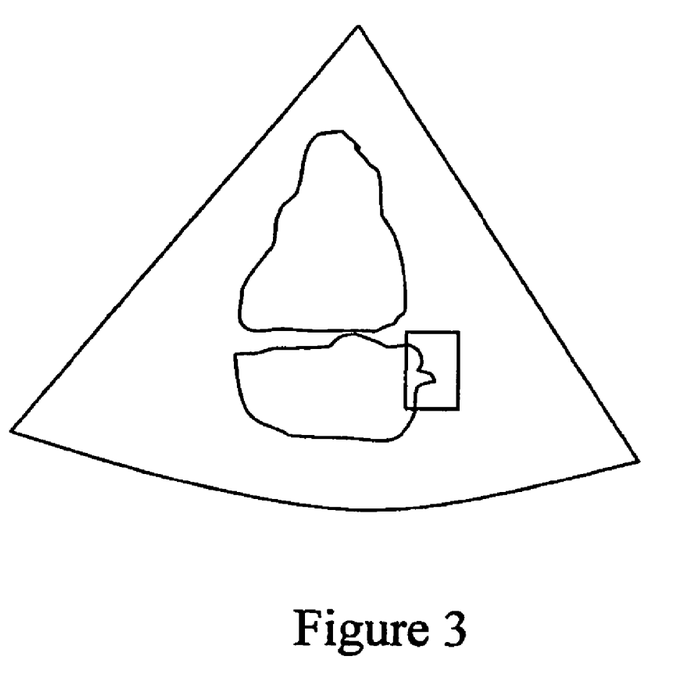
FIG. 3 is a graphical representation of a medical image in one embodiment.

For example, medical diagnostic ultrasound imaging systems have beamformer, filter, detection, scan conversion, or other types of imaging parameters. For imaging flow or tissue motion, an ultrasound imaging system operates based on a color pan box and/or a Doppler gate. For two- or three-dimensional imaging, velocity, energy and/or variance are estimated for a region. The color pan box defines the region, such as positioning the color pan box over a valve, chamber or other location. The template or other output from the classifier is used to locate specific structure not identified by classification. FIG. 3 shows a color pan box over a valve of the A2C view. Based on the color pan box and/or the type of anatomical information being imaged, the transmit and receive beam sequence, focal positions, scan format, apodization, waveform type, detection type, clutter filter, and/or other imaging parameters are set.

For spectral Doppler imaging, a Doppler gate is positioned in a region of interest. For example, the Doppler gate is positioned adjacent to a valve. The position of the Doppler gate indicates settings for the beam locations and spectral Doppler processing.

Other imaging parameters include B-mode imaging parameters. By identifying the anatomy of interest, the depth of B-mode scanning may be set to include the region of interest and minimize depth. The scan sequence, inter-line delay, frequency and/or other imaging parameters are set based on the depth.

One or more imaging parameters are set. Other imaging parameters may remain the same, be set based on other input, be manually adjusted, or be automatically adjusted. In one embodiment, a preset or group of imaging parameter values are automatically set as a function of the anatomical information. Any parameters or functions may be performed as a function of the anatomical information, such as disclosed in U.S. Pat. No. 7,092,749, the disclosure of which is incorporated herein by reference.

In act 34, subsequent imaging is performed based, at least in part, on the settings of act 32. The imaging is performed with the medical diagnostic system and is responsive to the imaging values set as the function of the anatomical feature. The imaging is performed during an imaging session. An imaging session typically occurs during a 15-60 minute time period for ultrasound imaging of a particular location during a patient visit. Imaging sessions may be longer or shorter and for imaging more than one location or for more than one diagnosis. Acts 22, 26, 32 and 34 may occur during a same imaging session. In one embodiment, the classification occurs in real-time, such as taking seconds (e.g., 1-2 seconds on a PC with a 2 GHz CPU and a 2 GB memory to classify a sequence which typically contains a full cardiac cycle with about 30 frames). The imaging parameters are set as a function of anatomical information, and imaging is performed substantially immediately after classification. Alternatively, the classification occurs off-line or after scanning or imaging. The imaging parameters are set for later acquisition and/or image processing of the previously acquired images.

In another embodiment, the identification of the anatomical information is used to set measurements. For example, a distance between two identified locations is measured as a function of identification of structure associated with the two locations. Volume, maximum value, minimum value, area, derivatives, integrals, or other values may be calculated automatically as a function of identifying the anatomical information.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

We claim:

1. A method for controlling a medical diagnostic ultrasound imaging system, the method comprising:

obtaining an ultrasound image;

identifying, with a processor and trained classifier, an anatomical feature in the ultrasound image;

setting, with the processor, an imaging value as a function of the anatomical feature; and subsequently imaging with the medical diagnostic ultrasound system, the imaging responsive to the imaging value set as the function of the anatomical feature;

wherein identifying the anatomical feature comprises extracting the anatomical feature with a multi-class classifier; wherein extracting comprises applying the multi-class classifier with feature vectors selected using a boosting framework sharing features at each round of boosting and applying the multi-class classifier with tree and cascade structures, the tree structure having a first node corresponding to separating a first class from a merger of remaining classes and a second node corresponding to separating at least two of the remaining classes.

2. The method of claim 1 wherein identifying comprises identifying a canonical view.

3. The method of claim 1 wherein setting comprises setting a beam location for a color pan box, a Doppler gate or both.

4. The method of claim 1 wherein setting comprises setting a B-mode display depth, a B-mode frequency, or both.

5. The method of claim 1 wherein identifying and setting are performed during an imaging session substantially in real-time, and wherein subsequently imaging is performed during the imaging session.

6. In a computer readable storage medium having stored therein data representing instructions executable by a programmed processor for controlling a medical imaging system, the storage medium comprising instructions for:

deriving anatomical information from a medical image with machine-learned feature vectors; and setting at least one imaging parameter of the medical imaging system as a function of the anatomical information, wherein deriving the anatomical information comprises extracting the anatomical information with a multi-class classifier; wherein extracting comprises applying the multi-class classifier with the machine-learned feature vectors selected using a boosting framework sharing features at each round of boosting and applying the multi-class classifier with tree and cascade structures, the tree structure having a first node corresponding to separating a first class from a merger of remaining classes and a second node corresponding to separating at least two of the remaining classes.

7. The instructions of claim 6 wherein deriving comprises deriving the anatomical information from a medical diagnostic ultrasound image, and wherein setting comprises setting the at least one imaging parameter of a medical diagnostic ultrasound imaging system.

8. The instructions of claim 6 wherein deriving comprises identifying cardiac structure associated with a particular view of a heart.

9. The instructions of claim 6 wherein deriving comprises identifying a heart valve, and wherein setting comprises positioning a color pan box, a Doppler gate or both for subsequent images.

10. The instructions of claim 6 wherein deriving and setting are performed during an imaging session substantially in real-time, images obtained in the imaging session responsive to the at least one imaging parameter set as a function of the anatomical information.

11. The instructions of claim 6 wherein setting comprises setting a B-mode display depth, a B-mode frequency, or both as a function of the anatomical information.

12. A medical diagnostic imaging system, the imaging system comprising:

a memory operable to store a medical image; and a processor operable to apply a classifier based on machine learning to the medical image, the classifier operable to identify a canonical view, tissue structure, flow pattern or combinations thereof from the medical image, the processor operable to control imaging as a function of the view, structure, pattern or combination thereof, wherein the classifier comprises a multi-class classifier with a tree and cascade structure, the tree structure having a first node corresponding to separating a first class from a merger of remaining classes and a second node corresponding to separating at least two of the remaining classes; and wherein the processor is configured to apply the multi-class classifier with feature vectors selected using a boosting framework sharing features at each round of boosting.

13. The imaging system of claim 12 wherein the processor comprises medical diagnostic ultrasound imaging system processor, the medical image comprises an ultrasound image, and the processor being operable to control comprises positioning a color pan box, positioning a Doppler gate, setting a B-mode display depth, setting a B-mode frequency, or combinations thereof.

14. The imaging system of claim 12 wherein the classifier is operable to identify cardiac structure associated with a particular view of a heart.

15. A method for identifying information from a medical image, the method comprising:

applying a multi-class classifier to the medical image, the multi-class classifier having a tree and cascade structure; and identifying a particular canonical view, tissue structure, flow pattern or combinations thereof from the medical image as a function of applying the multi-class classifier, wherein the applying comprises applying the multi-class classifier with feature vectors learned from boosting, and wherein the tree structure has a first node corresponding to separating a first class from a merger of remaining classes and a second node corresponding to separating at least two of the remaining classes.

16. The method of claim 15 further comprising:

automatically setting imaging parameters of an imaging system as a function of the particular canonical view, tissue structure, flow pattern or combination thereof.

17. In a computer readable storage medium having stored therein data representing instructions executable by a programmed processor for identifying information from a medical image, the storage medium comprising instructions for:

applying a multi-class classifier, with tree and cascade structures to the medical image; and identifying a particular canonical view, tissue structure, flow pattern or combinations thereof from the medical image as a function of applying the multi-class classifier, wherein identifying comprises extracting an anatomical feature with the multi-class classifier; wherein extracting comprises extracting applying the multi-class classifier with feature vectors selected using a boosting framework sharing features at each round of boosting and, the tree structure having a first node corresponding to separating a first class from a merger of remaining classes and a second node corresponding to separating at least two of the remaining classes.

18. The method of claim 1 wherein identifying comprises extracting a valve location with, the multi-class classifier in the tree and cascade structures such that the multi-class classifier is operable to simultaneously detect and classify multiple objects while rejecting background classes, and wherein setting comprises setting a color pan box, Doppler gate or both at the valve location.

* * * * *